(12) United States Patent
Meyerson et al.

(10) Patent No.: US 12,387,824 B2
(45) Date of Patent: Aug. 12, 2025

(54) PATIENT MANAGEMENT BASED ON SENSED INPUTS

(71) Applicant: Hill-Rom Services, Inc., Batesville, IN (US)

(72) Inventors: Craig M. Meyerson, Syracuse, NY (US); Eric P Jensen, Batesville, IN (US); Stacey Ann Fitzgibbons, DeWitt, NY (US); Jotpreet Chahal, Batesville, IN (US); Kirsten Emmons, Montgomery, IN (US); Lori Ann Zapfe, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 883 days.

(21) Appl. No.: 17/005,935

(22) Filed: Aug. 28, 2020

(65) Prior Publication Data

US 2021/0065856 A1 Mar. 4, 2021

Related U.S. Application Data

(60) Provisional application No. 62/894,388, filed on Aug. 30, 2019.

(51) Int. Cl.
| | | |
|---|---|---|
| *G16H 10/65* | (2018.01) | |
| *G16H 20/10* | (2018.01) | |
| *G16H 40/67* | (2018.01) | |
| *H04W 4/02* | (2018.01) | |

(52) U.S. Cl.
CPC ............ *G16H 10/65* (2018.01); *G16H 20/10* (2018.01); *G16H 40/67* (2018.01); *H04W 4/023* (2013.01)

(58) Field of Classification Search
None
See application file for complete search history.

(56) References Cited

U.S. PATENT DOCUMENTS

| | | | | |
|---|---|---|---|---|
| 2005/0285732 A1* | 12/2005 | Sengupta | ............... | G08B 21/02 340/309.7 |
| 2009/0105552 A1* | 4/2009 | Nishiyama | ............. | G16H 40/67 600/300 |
| 2010/0315225 A1* | 12/2010 | Teague | ................... | H04W 4/38 340/539.12 |
| 2011/0319726 A1* | 12/2011 | Sachanandani | ...... | A61B 5/0031 600/301 |

(Continued)

*Primary Examiner* — Devin C Hein
(74) *Attorney, Agent, or Firm* — Lee & Hayes, P.C.

(57) ABSTRACT

This disclosure is directed towards a patient management system for selectively storing and/or sharing patient data. A wearable device may sense a condition associated with the wearer of the wearable device, and store values based on the condition for a period of time. The wearable device may determine that the wearable device is within range of another device, such that the wearable device can communicate with the other device, and output the values to the other device. Additionally, a computing device of the patient management system may receive, from a wearable device, first data associated with a condition of a wearer of the wearable device. The computing device may also receive second data associated with the condition from a sensing device. The computing device may determine a context of the wearer based on comparing the first and second data, and control output of an alert based on the context.

20 Claims, 9 Drawing Sheets

(56) References Cited

U.S. PATENT DOCUMENTS

| | | | | |
|---|---|---|---|---|
| 2014/0207686 A1* | 7/2014 | Experton | ................ | G06F 21/31 |
| | | | | 705/51 |
| 2015/0288797 A1* | 10/2015 | Vincent | ................. | G16H 10/60 |
| | | | | 455/404.2 |
| 2018/0054710 A1* | 2/2018 | Gum | .................. | G09B 19/0092 |
| 2018/0256076 A1* | 9/2018 | Friedman | .............. | A61B 5/1113 |

* cited by examiner

PATIENT MANAGEMENT BASED ON SENSED INPUTS

CROSS REFERENCE TO RELATED APPLICATIONS

This application claims priority to U.S. Patent Application No. 62/894,388, filed Aug. 30, 2019, titled "PATIENT MANAGEMENT BASED ON SENSED INPUTS," the entire contents of which are incorporated herein by reference.

TECHNICAL FIELD

This application is directed to a patient management system, and in particular, to a system configured to selectively store and/or share patient data.

BACKGROUND

Activities undergone by a person may affect health outcomes in a variety of ways. For example, exercise, sleep, diet, and medications taken by a person may contribute to the health of the person. Collection and distribution of information regarding activities that affect a person's health may, at times, present challenges. For example, a person may not fully and/or accurately describe such activities when talking to a doctor, which may adversely affect how the doctor diagnoses and/or treats the person. Furthermore, sharing of the person's health data between different clinicians is often overlooked, which may further compound negative outcomes for the person.

The various example embodiments of the present disclosure are directed toward overcoming one or more of the deficiencies associated with patient management systems.

SUMMARY

Broadly, the systems and methods disclosed and contemplated herein are directed towards a patient management system for selectively storing and/or sharing patient data. In some examples, a wearable device may sense, by one or more sensors of the wearable device, a condition associated with the wearer of the wearable device. The wearable device may store values based on the condition for a period of time. The wearable device may determine that the wearable device is within a range of another device, such that the wearable device can communicate with the other device. The wearable device may output the values based on the condition of the wearer, a likely condition of the wearer, a need of the wearer, a position of the wearer, and so forth to the other device. Further, in some examples, a computing device of a patient management system may receive, from a wearable device, first data associated with a condition of a wearer of the wearable device. The computing device may also receive second data associated with the condition of the wearer from a sensing device. The computing device may determine a context of the wearer (e.g., a location, a pose, an activity being performed, change in a condition, etc.) based at least in part on comparing the first data and the second data, and may control an output of an alert based on the context. The computing device may perform the comparing (or "patient baselining") based on a condition of the patient in the patient's unique homeostatic state compared to a deterioration of the condition, when the patient is in a crisis situation, and so on.

DETAILED DESCRIPTION

Figure 1:
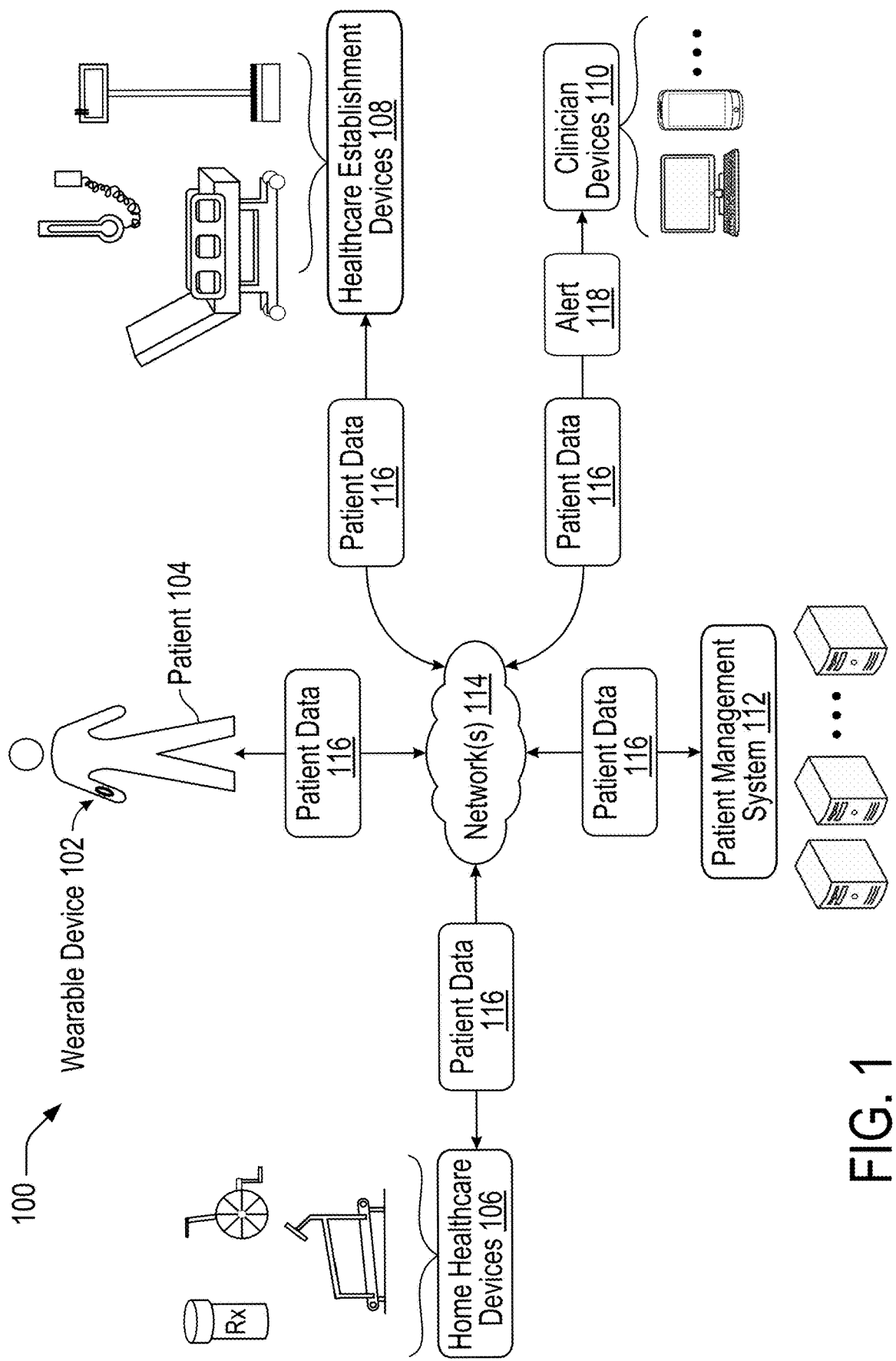
FIG. 1 shows a schematic block diagram of an example patient management system environment.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

FIG. 1 shows a schematic block diagram of an example patient management system environment 100. The example patient management system environment 100 includes at least one wearable device 102 (e.g., worn by a patient 104, where the patient 104 may also be referred to as a "wearer" of the wearable device 102), one or more home healthcare devices 106, one or more healthcare establishment devices 108, one or more clinician devices 110, and a patient management system 112. The wearable device 102, the home healthcare devices 106, the healthcare establishment devices 108, the clinician devices 110, and/or the patient management system 112 may be in communication via one or more networks 114.

In some examples, the wearable device 102 may be any suitable portable computing device that can store data and being transported by the patient 104, such as a watch, a necklace, a ring, a bracelet, eyeglasses, shoe(s), clothing, a patch, a belt, a band, and/or other type of accessory. Examples are also contemplated in which the wearable device 102 comprises a phone, tablet, laptop computer, or other computing device that may not necessarily be "worn" on the body of the patient 104. In some cases, the wearable device 102 may include one or more sensors, such as a heartrate sensor, respiration sensor, glucose sensor, blood pressure sensor, diagnostic sensor, activity sensor (e.g., accelerometer, gyroscope, etc.), and so forth.

The home healthcare devices 106 may include devices that the patient 104 interacts with that may impact and/or monitor the health of the patient 104. For instance, the home healthcare devices 106 may include tools that the patient 104 may interact with in the consumption of medication. In but one specific example, prescription and/or non-prescription medication containers may include sensors to determine whether the patient 104 has taken (or not taken) a medication, and/or a dosage of the medication that the patient 104 has taken. For example, if the wearable device 102 is on the wrist of the patient 104 and comes within a threshold distance (e.g., six inches, twelve inches, etc.) of a prescription medication container having an RFID tag, an RFID sensor in the wearable device 102 may register that the patient has opened the prescription medication container. The wearable device 102 may store this information along with a time stamp, which may indicate that the patient 104 has taken a dose of the prescription medication at a particular time. Similarly, such information may indicate that the patient 104 has missed a dose of the prescription medication if the RFID sensor of the wearable device 102 has not registered being within the threshold distance of the RFID tag within a duration of time associated with the dosage schedule of the prescription medication. In such a case where a missed dose is detected, the wearable device 102 may output a reminder to the patient 104, and/or send an instruction to another device (e.g., a mobile phone or tablet device of the patient 104) to remind the patient 104 to perform the prescribed action. Other medication consumption devices are considered as well, such as inhalers, syringes, eye and/or ear drops, sprays, patches, pumps, and so forth.

The home healthcare devices 106 may include other device types as well. In some examples, the home healthcare devices 106 may include exercise devices, such as treadmills, bicycles (stationary or mobile), weightlifting equipment, bodyweight exercise equipment, and the like. Exercise devices may to track and/or record exercises and/or other physical activity of the patient 104, and may be configured to transmit information regarding exercise performed by the patient 104 to the wearable device 102. Additionally, the home healthcare devices 106 may include patient assistance devices, such as wheelchairs, scooters, walkers, crutches, prosthetic devices, orthotic devices, hearing aids, cognitive aids, and so on. Even further, the home healthcare devices 106 may include devices that assist the patient 104 with their diet, such as a food scale and/or a mobile device that includes a camera with which the patient 104 can take written notes, images, and/or video of what the user eats. In some examples, the home healthcare devices 106 may include health monitoring devices such as a bodyweight scale, bodyfat measurement tool, hydration measurement tool, bone density measurement tool, and the like. In some examples, the home healthcare devices 106 may include sensors for detecting trips to a restroom (e.g., a sensor in/proximate a toilet or sink), a fall sensor to determine if the patient 104 has fallen down, a mattress sensor or mat for sleep pattern and/or mobility pattern detection, and the like. In some cases, the home healthcare devices 106 may comprise a tablet, mobile phone, laptop computer, desktop computer, or other computing device that includes an application enabling the patient 104 to input self-reported conditions or outcomes, which in turn may be shared with the wearable device 102.

In some examples, the healthcare establishment devices 108 may include devices that generally exist in a healthcare establishment (e.g., doctor's office, hospital, clinic, dentist's office, pharmacy, ambulance, and the like) that may impact and/or monitor the health of the patient 104. For instance, the healthcare establishment devices 108 may include blood pressure devices, $SpO_2$ devices, temperature devices, respiratory devices, bodyweight scales, otoscopes, ophthalmoscopes, stethoscopes, vision screening devices, hearing screening devices, microscopes, ECG devices, beds and other furniture, and so on. While the healthcare establishment devices 108 are described as existing within a healthcare establishment, examples are considered in which such devices may be found outside of a healthcare establishment, in some cases.

In examples, the clinician devices 110 may include computing devices such as mobile phones, tablet computers, laptop computers, desktop computers, and so forth which provide a clinician (e.g., a doctor, nurse, technician, pharmacist, dentist, etc.) with information about the health of the patient 104. In some cases, the clinician devices 110 may exist within a healthcare provider establishment (e.g., alongside the healthcare establishment devices 108), although examples are also considered in which the clinician devices 110 exist and/or are transported outside of a healthcare provider establishment, such as a doctor's mobile phone or home desktop computer that the doctor may use when the doctor is on-call. Alternatively or additionally, the clinician devices 110 may include devices used in emergency medical situations (e.g., in an ambulance and/or accessible by emergency medical technicians (EMTs)), where the clinician devices in these situations can add, remove, change, and/or otherwise access data stored on the wearable device 102. Permitting the clinician devices 110 to access the data stored on the wearable device may provide relevant and important information regarding the patient 104 in emergency situations to the EMTs, and pass information collected during an emergency to other clinicians in a seamless manner.

The wearable device 102, the home healthcare devices 106, the healthcare establishment devices 108, and/or the clinician devices 110 may include a processor, microprocessor, and/or other computing device components, shown and described below. For instance, the wearable device 102, the home healthcare devices 106, the healthcare establishment devices 108, and/or the clinician devices 110 may be configured as mobile phones, tablet computers, laptop computers, etc., to deliver or communicate the patient data 116 amongst one another and to other devices.

The patient management system 112 may be comprised of one or more server computing devices, which may communicate with the wearable device 102, the home healthcare devices 106, the healthcare establishment devices 108, and/or the clinician devices 110 to respond to queries, receive data, and so forth. Communication between the patient management system 112, the wearable device 102, the home healthcare devices 106, the healthcare establishment devices 108, and/or the clinician devices 110 occurs via the network 114, where the communication can include patient data 116 related to the health of the patient 104. A server of the patient management system 112 can act on these requests from the wearable device 102, the home healthcare devices 106, the healthcare establishment devices 108, and/or the clinician devices 110, determine one or more responses to those queries, and respond back to the wearable device 102, the home healthcare devices 106, the healthcare establishment devices 108, and/or the clinician devices 110. A server of the patient management system 112 may also include one or more processors, microprocessors, or other computing devices as discussed in more detail in relation to FIG. 9.

The patient management system 112 may include one or more database systems accessible by a server storing different types of information. For instance, a database can store correlations and algorithms used to manage the patient data 116 to be shared between the wearable device 102, the home healthcare devices 106, the healthcare establishment devices 108, and/or the clinician devices 110. A database can also include clinical data. A database may reside on a server of the patient management system 112 or on separate computing device(s) accessible by the patient management system 112.

The network 114 is typically any type of wireless network or other communication network known in the art. Examples of the network 114 include the Internet, an intranet, a wide area network (WAN), a local area network (LAN), and a virtual private network (VPN), cellular network connections and connections made using protocols such as 802.11a, b, g, n and/or ac. Alternatively or additionally, the network 114 may include a nanoscale network, a near-field communication network, a body-area network (BAN), a personal-area network (PAN), a near-me area network (NAN), a campus-area network (CAN), and/or an inter-area network (IAN).

In some examples, the patient management system 112, the wearable device 102, the home healthcare devices 106, the healthcare establishment devices 108, and/or the clinician devices 110 may generate, store, and/or selectively share the patient data 116 between one another to provide the patient 104 and/or clinicians treating the patient 104 with improved outcomes by providing a holistic picture of the health of the patient 104. For instance, the wearable device 102 sense a condition associated with the patient 104, such as a heart rate, heart rate variability, respiratory rate, sleep patterns, blood glucose readings, blood pressure, ECG waveforms, movement, mobility, hydration (e.g., via impedance), capillary refill, biomarkers (e.g., via an interstitial patch), pressure injury risk, and so forth, and store patient data 116 in the form of values associated with the condition for at least a period of time. The period of time may be a predetermined time (e.g., 1 day, 3 days, one week, one month, etc.), or a variable time (e.g., between clinician visits, until stopped by the patient 104, etc.). The patient management system 112 may determine trends associated with the condition of the patient 104 over the period of time.

In some cases, the wearable device 102 may determine that the wearable device is within a range of one or more of the home healthcare devices 106, the healthcare establishment devices 108, and/or the clinician devices 110, such that the wearable device 102 is able to communicate the patient data 116 to and/or from the other device(s). For instance, the wearable device 102 may be transported by the patient 104 into a local area network to which a clinician device 110 is connected and facilitates communication between the wearable device 102 and the clinician device 110. The wearable device 102 may output patient data 116, including values associated with a condition of the wearer collected as described above, via the local area network (or other network 114) to the clinician device 110. The clinician device 110 may then use the patient data 116 received from the wearable device 102 to update an electronic medical record (EMR) for the patient 104, provide a baseline associated with the condition of the patient 104, and so forth. In some examples, the EMR of the patient 104 includes a medical history of the patient 104.

In some examples, the wearable device 102 may share the patient data 116 with a healthcare establishment device 108, such as by outputting values associated with a condition of the patient 104 to the healthcare establishment device 108 and/or receiving values associated with the condition of the patient 104 in patient data 116 from the healthcare establishment device 108. The wearable device 102 may compare values for the condition as sensed by a sensor of the wearable device 102 with values received from the healthcare establishment device 108 to determine accuracy of the values sensed by the sensor of the wearable device 102, to calibrate the wearable device 102, determine a context of the patient (as discussed in more detail below), and so forth. The wearable device 102 may control an output of one or more alerts 118 based on a difference between the values, such as providing an instruction to output an alert 118 to a clinician device 110 and/or preventing an alert 118 from being output to the clinician device 110. For instance, the healthcare establishment device 108 may detect that a heart rate of the patient 104 is elevated, and thus may attempt to output an alert 118 to a clinician device 110 to alert a clinician of the elevated heart rate condition of the patient 104. However, the wearable device 102 may determine that the patient 104 has undergone a walk around a floor of a hospital where the patient 104 is admitted, and thus determine that the heart rate of the patient 104 is expected to be elevated. The wearable device 102 may prevent the alert 118 from being output to the clinician device 110, thereby preventing the clinician from being unnecessarily alerted based on the context of the patient 104.

Further, in some examples, the patient management system 112 may take part in storing and/or controlling how the patient data 116 is shared between the wearable device 102, the home healthcare devices 106, the healthcare establishment devices 108, and/or the clinician devices 110. For instance, the patient management system 112 may receive the patient data 116 from the wearable device 102, which may include data relating to a condition sensed by the wearable device 102, an EMR of the patient 104, and so forth. The patient management system 112 may also receive patient data 116 associated with a condition of the patient 104 from the home healthcare devices 106, the healthcare establishment devices 108, and/or the clinician devices 110. The patient management system 112 may determine a context of the patient 104 from the different sources of the patient data 116, and may control output of the alert 118 based on the context. In some examples, the patient management system 112 may control the output of the alert 118 by selecting, from multiple clinician devices 110, which clinician device to send an alert to. For instance, if a healthcare establishment device 108 such as a SpO$_2$ monitor of the patient 104 outputs a reading of low oxygen saturation, while the wearable device 102 is outputting a normal oxygen saturation, the patient management system 112 may cause an alert 118 to be output to a nurse assistant to check the positioning of the SpO$_2$ monitor on the patient 104 rather than alerting a doctor or nurse of a false emergency situation. The patient management system 112 may also control redundancy of alerts (e.g., preventing an alert from unnecessarily repeating, preventing an alert from being sent to multiple devices when not necessary, and so forth).

In some examples, the patient management system 112 may compile data collected from the various devices into trends associated with the patient 104. For instance, access to raw data regarding a condition may be overwhelming for both the patient 104 and/or a clinician treating the patient 104. Therefore, the patient management system 112 may select different time periods to average data for a trends for different conditions (e.g., an average fasting blood sugar over a one-week period sensed each morning of the particular week, a change in blood pressure over the course of a month, a change in sleep patterns over the course of a year, etc.), and may also be configured to select data that may be relevant to the patient 104 or a clinician treating the patient based on irregularities, normal conditions, and the like.

Example configurations of the wearable device 102, the home healthcare devices 106, the healthcare establishment devices 108, and/or the clinician devices 110, and methods for their use, are shown and described with reference to at least FIGS. 2-9 below.

Figure 2:
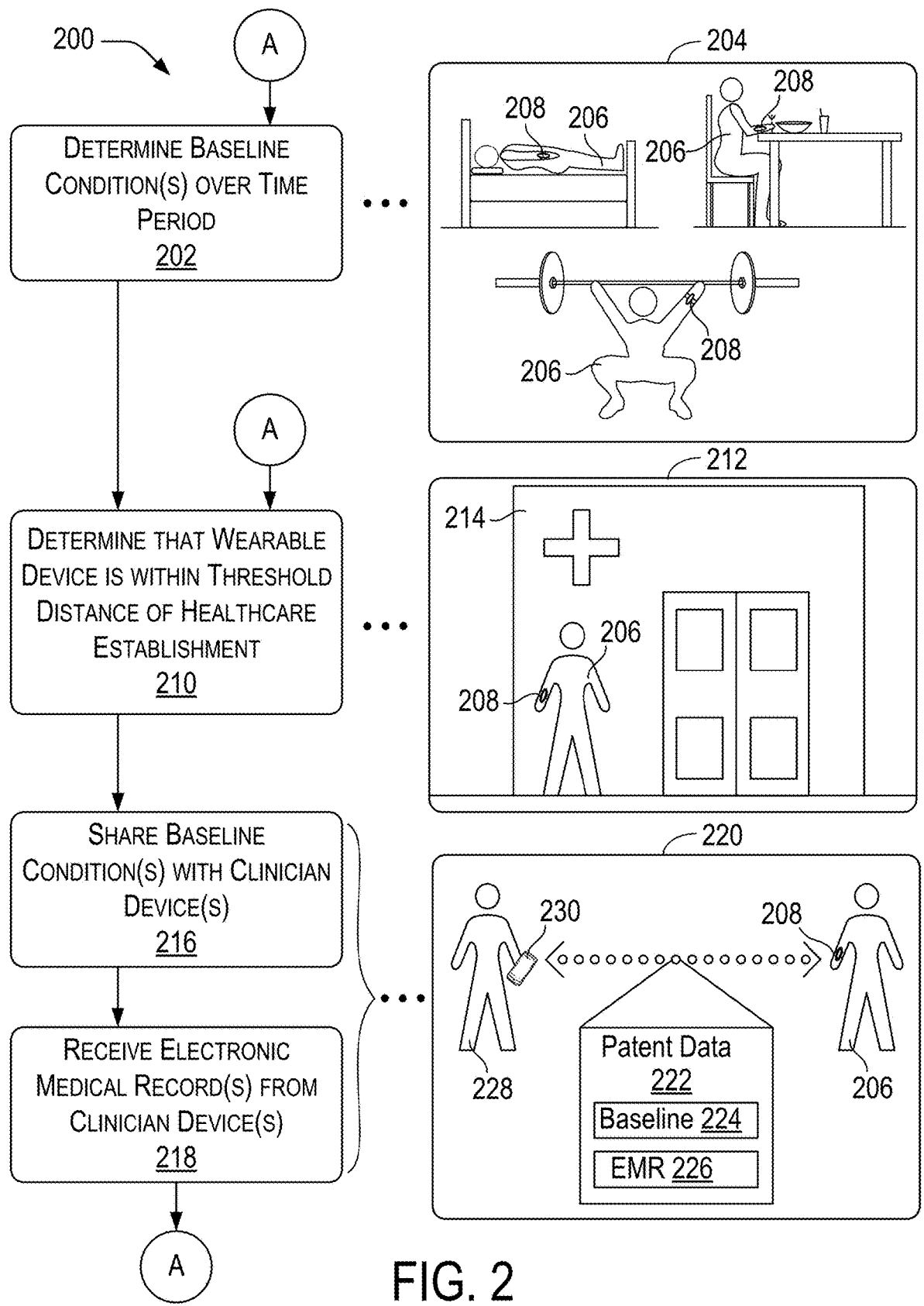
FIG. 2 is a pictorial flow diagram illustrating the use of a wearable device to control storage and sharing of patient data.

FIG. 2 is a pictorial flow diagram 200 illustrating the use of a wearable device to control storage and sharing of patient data. An operation 202 includes determining one or more baseline conditions over a time period. A representation 204 depicts a wearer 206 of a wearable device 208 undertaking a number of activities. The wearable device 208 may include, and/or be in communication with, one or more sensors that sense parameter(s) associated with condition(s) of the wearer 206. In examples, the sensors may sense conditions of the wearer 206 as the wearer goes about their daily activities, such as sleeping, eating, exercising, taking medications, and so forth. As described herein, the condition(s) may include heart rate, respiration, blood pressure, blood glucose, sleep patterns, exercise patterns, eating patterns, medication consumption, and so on. The wearable device 208 may establish a baseline condition by sensing the condition(s) over a period of time (e.g., one day, three days, one week, one month, between clinician visits, etc.). In some cases, the wearable device 208 may establish the baseline condition by averaging values associated with the sensed condition over the period of time.

An operation 210 includes determining that the wearable device is within a threshold distance of a healthcare establishment. A representation 212 depicts the wearer 206 of the wearable device 208 approaching a healthcare establishment 214, such as a hospital or doctor's office. In some examples, the wearable device 208 may determine proximity to the healthcare establishment 214 by detecting a network of the healthcare establishment, such as a LAN, Wi-Fi network, and the like. Alternatively or additionally, the wearable device 208 may detect one or more other devices of the healthcare establishment 214, such as the healthcare establishment devices 108 and/or the clinician devices 110 of FIG. 1, and from this information may determine that the wearable device 208 is near or within the healthcare establishment 214. In some cases, the wearable device 208 may determine a location of the wearer 206 of the wearable device 208 relative to the healthcare establishment 214 using localization techniques, such as GPS. The threshold distance may be a predetermined distance relative to the healthcare establishment 214, such as one meter from a door of the healthcare establishment 214, within the door of the healthcare establishment 214, within a patient waiting room of the healthcare establishment 214, or within an exam room of healthcare establishment 214, to name a few examples. The threshold distance may, in some examples, be a sufficient distance such that the wearable device 208 does not share data with devices within the healthcare establishment 214 if the wearer 206 is commuting past the healthcare establishment 214, such as by walking on a sidewalk or driving a car on the street outside of the healthcare establishment 214.

An operation 216 includes sharing the one or more baseline conditions with one or more clinician devices of the healthcare establishment. Further, an operation 218 includes receiving one or more electronic medical records from the one or more clinician devices healthcare establishment. A representation 220 depicts the wearable device 208 sharing patient data 222 (e.g., wirelessly via a network as described in relation to FIG. 1) with a clinician device 230. As shown, the patient data 222 includes baseline data 224, which may be generated and/or stored by the wearable device 208 prior to the wearer 206 entering the healthcare establishment 214. The clinician device 230 may alternatively, or in addition, share an EMR 226 of the wearer 206 with the wearable device 208. In some cases, the EMR 226 may include data generated by one or more healthcare establishment devices (e.g., a scale, blood pressure monitor, ECG, etc.) during a visit by the wearer to the healthcare establishment 214. Alternatively or additionally, the EMR 226 may include instructions provided by a clinician 228, such as medications, dosage amounts, dosage timing, referrals to other clinicians, exercises, activity recommendations, and so forth. In some examples, the EMR 226 may be stored in the wearable device 208, and may be accessible by the wearer 206 once received.

In some examples, the exchange of the patient data 222 in the operations 216 and/or 218 may occur automatically, e.g., without being initiated by the wearer 206 of the wearable device 208 and/or the clinician 228. For instance, the proximity of the wearable device 208 to the clinician device 230, the healthcare establishment 214, and/or healthcare establishment devices within the healthcare establishment 214 (e.g., being within a threshold distance) may cause the exchange of the patient data 222. In this way, the clinician 228 may automatically receive the baseline data 224 (e.g., while the wearer 206 is in a waiting room of the healthcare establishment 214), have time to review the baseline data 224 prior to meeting with the wearer 206, and be prepared to discuss the baseline data 224 with and/or provide health recommendations to the wearer 206 during the wearer's visit to the healthcare establishment 214. In some examples, the wearable device 208 may share the patient data 222 a clinician device 230 that includes a display at which the wearer 206 and the clinician 228 can view trends or patterns of the baseline data 224 together (e.g., to facilitate discussion between the wearer 206 and the clinician 228 regarding one or more conditions of the wearer 206). Furthermore, the automatic exchange of the patient data 222 may provide the clinician 228 with insight regarding one or more conditions of the wearer 206 if the wearer arrives at the healthcare establishment 214 in an unconscious state, or is otherwise unable to adequately communicate with the clinician 228 regarding the condition(s) of the wearer 206.

In examples, the process may return to operation 202 and/or operation 210 (via "A") following the visit by the wearer 206 to the healthcare establishment 214. For example, upon conclusion of the visit to the healthcare establishment 214, the wearable device 208 may determine a new baseline condition of the wearer 206 in operation 202 in view of changes to the EMR 226 of the wearer 206. The wearable device 208 may initiate collecting sensor data for the new baseline condition in response to the wearer 206 exiting the healthcare establishment 214, as indicated by the wearable device 208 no longer having a communication connection with the network of the healthcare establishment 214, or upon receiving an indication from a device within the healthcare establishment 214 that the baseline data 224 has been received. In some examples, the wearable device 208 may remove the baseline data 224 from memory, and/or store the baseline data 224 in an alternate location (e.g., a cloud storage system) to allow for new sensor data associated with the baseline condition.

In some cases, the wearer 206 may visit another location within the same healthcare establishment 214 and/or a different healthcare establishment, by which the wearable device 208 may determine that it is within a threshold distance of the next healthcare establishment by operation 210. In some examples, the wearable device 208 may determine proximity to the next healthcare establishment by detecting a network of the healthcare establishment, such as a LAN, Wi-Fi network, and the like. Alternatively or additionally, the wearable device 208 may detect one or more other devices of the next healthcare establishment, such as the healthcare establishment devices 108 and/or the clinician devices 110 of FIG. 1, and from this information may determine that the wearable device 208 is near or within the next healthcare establishment. In some cases, the wearable device 208 may determine a location of the wearer 206 of the wearable device 208 relative to the next healthcare establishment using localization techniques, such as GPS, as described above. This may be the case when the wearer 206 enters a hospital emergency room, for instance, followed by a transfer of the wearer 206 to an acute care department of the hospital. In such a case, the wearable device 208 may store the patient data 222 (including the baseline data 224 and the EMR 226) as the wearer 206 is transferred from one healthcare establishment to another. In this way, the patient data 222 stays with the wearer 206 as the wearer is moved, thus reducing lost records, reducing the wearer 206 and/or a clinician from needing to repeat information between healthcare establishments (e.g., verbally or via paperwork), and maintaining consistent records of what happens to the wearer 206 both before the wearer enters the healthcare establishment 214 and throughout the stay of the wearer in different healthcare establishments, as discussed in more detail in relation to FIG. 3.

Figure 3:
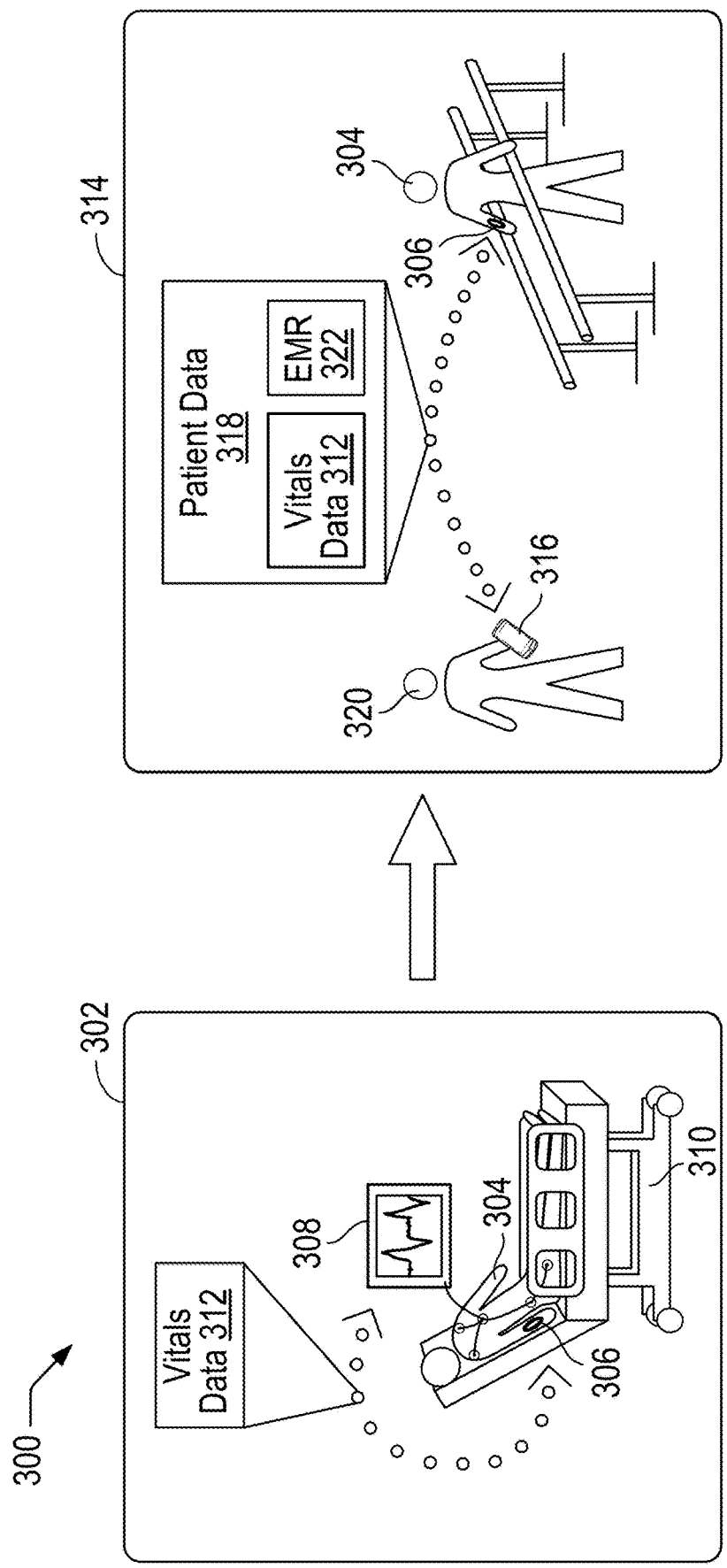
FIG. 3 is a pictorial flow diagram illustrating the use of a wearable device to control storage and sharing of patient data within a healthcare environment.

FIG. 3 is a pictorial flow diagram 300 illustrating the use of a wearable device to control storage and sharing of patient data within a healthcare environment.

A representation 302 depicts a wearer 304 (e.g., the patient 104 of FIG. 1 and/or the wearer 206 of FIG. 2) wearing a wearable device 306 (e.g., the wearable device 102 of FIG. 1 and/or the wearable device 208 of FIG. 2). In this example, the wearer 304 may have an ECG device 308 attached to the body of the wearer 304 by one or more sensors of the ECG device 308. Additionally, the wearer 304 may be in a hospital bed 310, which may be configured to sense one or more conditions of the wearer, such as presence of the wearer, position of the wearer (e.g., pose associated with sitting, standing, supine, etc.), movement of the wearer (e.g., whether the wearer has been turned by a clinician on a regular schedule, ingress and/or egress from the hospital bed, etc.), heart rate of the wearer, respiration rate of the wearer, and so forth. The ECG device 308 and the hospital bed 310 are representative of healthcare establishment devices, and it should be understood that any suitable healthcare establishment (or other device) may be used without departing from the scope of the disclosure.

In examples, the ECG device 308 may communicate vitals data 312 associated with the wearer 304 to the wearable device 306, such as responsive to determining that the wearable device 306 is within a threshold distance (e.g., one meter, five meters, ten meters, etc.) of the ECG device 308. In some cases, the ECG device 308 may require an authentication step prior to sharing the vitals data 312, such as verification by the wearer 304 and/or a clinician that the wearable device 306 is permitted to receive the vitals data 312. Similarly, although not explicitly pictured, the hospital bed 310 may communicate data associated with the wearer 304 to the wearable device 306 responsive to determining that the wearable device 306 is within a threshold distance (e.g., one meter, five meters, ten meters, etc.) of the hospital bed 310. The wearable device 306 and/or a patient management system may leverage data from multiple sources, such as the wearable device 306, the ECG device 308, and/or the hospital bed 310 to determine a context of the wearer 304, such as a location of the wearer, an activity being performed by the wearer (e.g. using a restroom, going for a walk, eating, etc.), and so forth. The wearable device 306 may store the vitals data 312 as part of, or in addition to, data relating to the context of the wearer 304.

In one specific example, the patient management system may determine a context of the wearer 304 using a respiration rate signal from the wearable device 306 and an oximeter reading from a $SpO_2$ device. If the respiration rate is normal (e.g., between 12 and 20 breaths per minute) as recorded by the wearable device 306, while the oximeter reading is zero (or a reading below a normal oximeter reading of 96% to 99%, for instance), the patient management system may route an alert to a technician in order to replace the $SpO_2$ sensor on the wearer. On the other hand, if both the respiration rate and the oximeter readings are zero, the patient management system may route an alert to a doctor or nurse to address the condition of the wearer.

A representation 314 depicts the wearer 304 in a different healthcare establishment such as a physical therapy setting, e.g., after the wearer 304 was discharged from the hospital and following a time that the wearer 304 was in the hospital bed 310 in the representation 302. Even though the wearer 304 is in a different healthcare establishment, the wearable device 306 may detect a clinician device 316 (e.g., being within a threshold distance of the clinician device), and may transmit patient data 318 related to the wearer 304 to the clinician device 316. The patient data 318 may include the vitals data 312 previously received by the wearable device 306 from the ECG device 308, discharge instructions, and the like. Therefore, a clinician 320 in a different healthcare establishment may view the vitals data 312 for the wearer 304 when the wearer 304 is present in the healthcare establishment, without having to request the data from the previous healthcare establishment where the ECG device 308 was located and wait for such data to be delivered. In some examples, the patient data 318 may also include an EMR 322, which may include data from the hospital bed 310 or other healthcare establishment devices, data from home healthcare devices, and so forth. For instance, the EMR 322 may include data from a physical therapy device in the home of the wearer 304, such as whether the wearer 304 completed home physical therapy exercises, when the wearer 304 completed the exercises, an intensity of the wearer 304 when undertaking the physical therapy exercises, and so on. Further, the clinician 320 may input instructions for additional physical therapy exercises to be conducted by the wearer 304 at home into the clinician device 316, which in turn may be included in the EMR 322, shared with the wearable device 306, and stored by the wearable device 306 for review by the wearer 304 and/or other clinicians.

Figure 4:
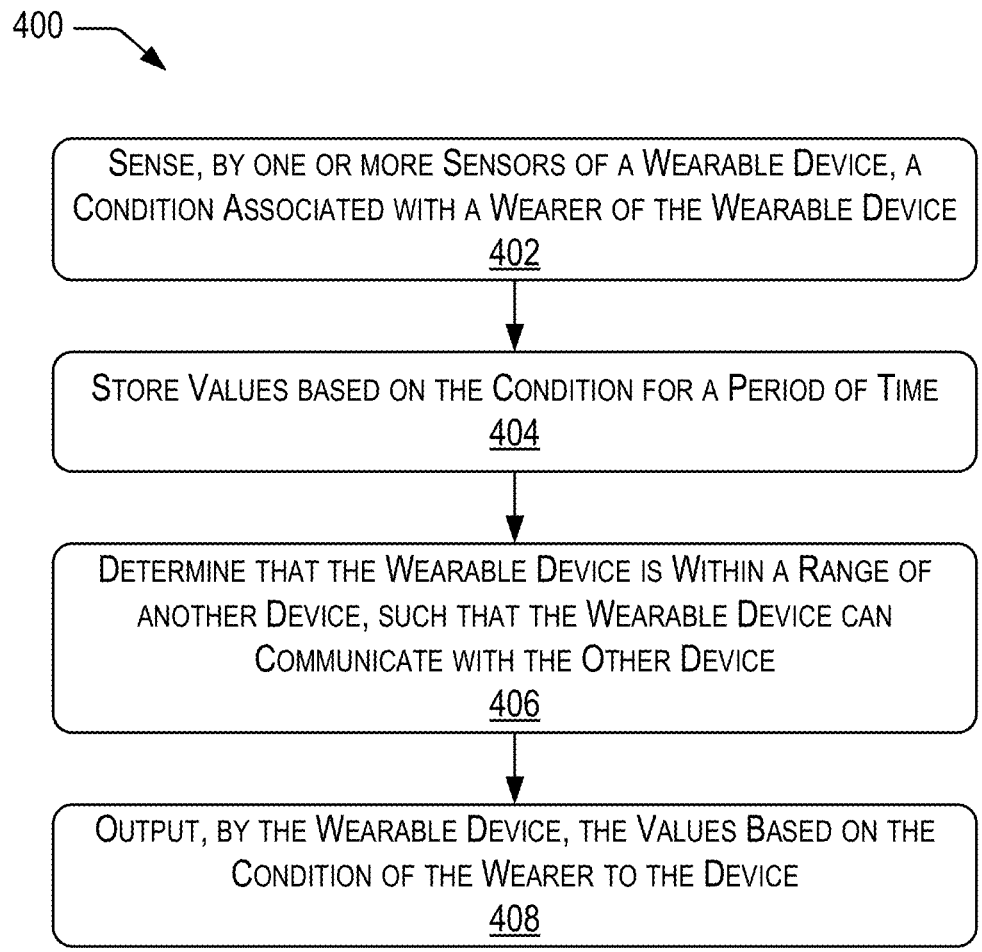
FIG. 4 is an example process for utilizing a wearable device to store and output patient data to another device, according to the techniques described herein.

FIG. 4 is an example process 400 for utilizing a wearable device to store and output patient data to another device, according to the techniques described herein. In some examples, one or more operations of the process 400 may be combined with one or more operations of the methods illustrated in FIGS. 5-8. In some examples, the process 400 may be performed by one or more processors of computing devices, such as the wearable device 102 of FIG. 1.

At operation 402, the process can include sensing, by one or more sensors of a wearable device, a condition associated with a wearer of the wearable device. As discussed above, the condition may include heart rate, respiratory rate, sleep patterns, blood glucose readings, blood pressure, movement, and so forth.

At operation 404, the process can include storing, by the wearable device, values indicative of the condition for a period of time. The period of time may be a predetermined period of time (e.g., one day, three days, one week, one month, etc.), and/or may be a variable period of time, such as between clinician visits, until an instruction to stop storing the values is received from the wearer or a clinician, until a condition is met (e.g., the values correspond to a baseline for the wearer), and so on.

At operation 406, the process can include determining, by the wearable device, that the wearable device is within a range of another device, such that the wearable device is able to communicate with the other device. For example, the other device may be a home healthcare device, a healthcare establishment device, and/or a clinician device, as discussed above. The wearable device may communicate with the other device using radio frequency, Bluetooth, a nanoscale network, a near-field communication network, a body-area network (BAN), a personal-area network (PAN), a near-me area network (NAN), a campus-area network (CAN), and/or an inter-area network (IAN). In some cases, the communication may occur responsive to scanning a QR code and/or a bar code associated with the wearable device, as well. The range that enables communication between the wearable device and the other device may depend upon the technique used to communicate and/or the type of network used for communication between the devices. The wearable device may be configured to communicate with different devices using different techniques, for instance, the wearable device may passively receive bodyweight data from an RF signal of the wearer's home scale when the wearer weighs herself, but may only pass on patient data and/or an EMR associated with the wearer responsive to scanning a specific QR code (e.g., to ensure patient privacy).

At operation 408, the process can include outputting, by the wearable device, the values indicative of the condition of the wearer of the device. The values may provide information about the wearer over time, so that when output, a clinician may better understand the health history of the wearer, and alerts or notifications may be appropriately controlled based on conditions specific to the wearer, as described above and below.

Figure 5:
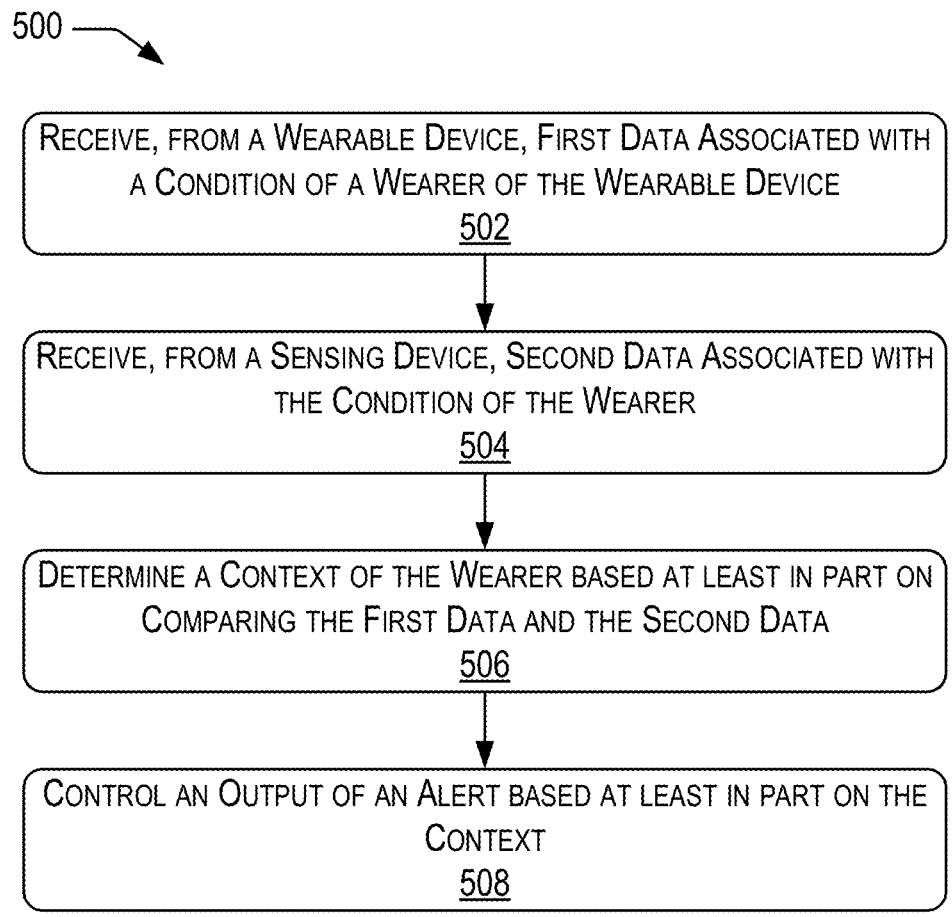
FIG. 5 is an example process for determining a context of a wearer based on data received from a wearable device and data received from a sensing device, according to the techniques described herein.

FIG. 5 is an example process 500 for determining a context of a wearer based on data received from a wearable device and data received from a sensing device, according to the techniques described herein. In some examples, one or more operations of the process 500 may be combined with one or more operations of the methods illustrated in FIGS. 4 and/or 6-8. In some examples, the process 500 may be performed by one or more computing devices, such as a computing device of the patient management system 112 of FIG. 1.

At operation 502, the process can include receiving, by one or more processors and from a wearable device, first data associated with a condition of a wearer of the wearable device. As discussed above, the condition may include heart rate, respiratory rate, sleep patterns, blood glucose readings, blood pressure, movement, and so forth. In some cases, the first data may correspond to a baseline condition of the wearer (e.g., outside of a healthcare establishment setting), and EMR of the wearer (e.g., including allergies, medications, etc.), data corresponding to the wearer while in a healthcare establishment (e.g., on a previous clinician shift, in a different department of the healthcare establishment, etc.), medical history of the wearer, and so forth.

At operation 504, the process can include receiving, by the one or more processors and from a sensing device, second data associated with the condition of the wearer. In some examples, the sensing device may be a home healthcare device, a healthcare establishment device, and/or a clinician device, as discussed above.

At operation 506, the process can include determining, by the one or more processors, a context of the wearer based at least in part on comparing the first data and the second data. For instance, because the wearable device captures data that the sensing device may not necessarily have access to, combining the data may provide a more holistic picture of the health care state of the wearer. In but one example, the wearer may be at risk of congestive heart failure, and thus may be instructed to weigh themselves daily. The home healthcare device (in this case, a bodyweight scale) may provide the weight of the wearer to the wearable device each time the wearer uses the bodyweight scale. Additionally, the wearable device may periodically check the wearer's blood pressure. Provided with information that the wearer is at risk for congestive heart failure, the wearable device may compare the bodyweight measurements received from the bodyweight scale along with the blood pressure measurements to determine a context of the condition of the wearer (e.g., that the condition is improving, that the condition is worsening, or that the condition is remaining the same). The wearable device may compare the bodyweight measurements and the blood pressure measurements responsive to an indication in the wearer's EMR of the risk of congestive heart failure, along with conditions in the EMR indicative of the condition changing such as bodyweight and blood pressure Additionally, in some examples, the wearable device may automatically obtain and/or assemble and analyze information from an EMR of the wearer that is relevant to a condition of the wearer, such as comorbidities, historical laboratory results/values, and the like. The wearable device may combine information included in the EMR with various information being input to the wearable device from sensors of the wearable device, home healthcare devices, clinician devices, and so on dynamically and/or in real time to monitor one or more conditions. In some cases, the wearable device may generate a health index score representing an overall health of the wearer and/or specific condition(s) of the wearer. The wearable device may compare the health index score of the wearer to a threshold, which may trigger an action (e.g., outputting an alert or notification), which may be dependent upon a clinical setting. As described above, the wearer may utilize an application on a mobile phone, tablet, laptop computer, desktop computer, or other computing device to input symptoms for conditions that are of clinical concern, as well.

At operation 508, the process can include controlling, by the one or more processors, an output of an alert based at least in part on the context. Continuing with the congestive heart failure example above, the wearable device may transmit an alert to a clinician if the wearer experiences a weight gain of more than five pounds in one week, along with an increase in blood pressure over the same time period. The output of alerts may be controlled based on an estimated error in condition monitoring by the wearable device and/or the sensing device, a severity of the condition of the wearer (e.g., which clinician to send an alert to, such as a doctor, a nurse, a nurse assistant, etc.), activity by the wearer that may cause an expected change to the condition (but would otherwise cause output of an alert), and so forth.

Figure 6:
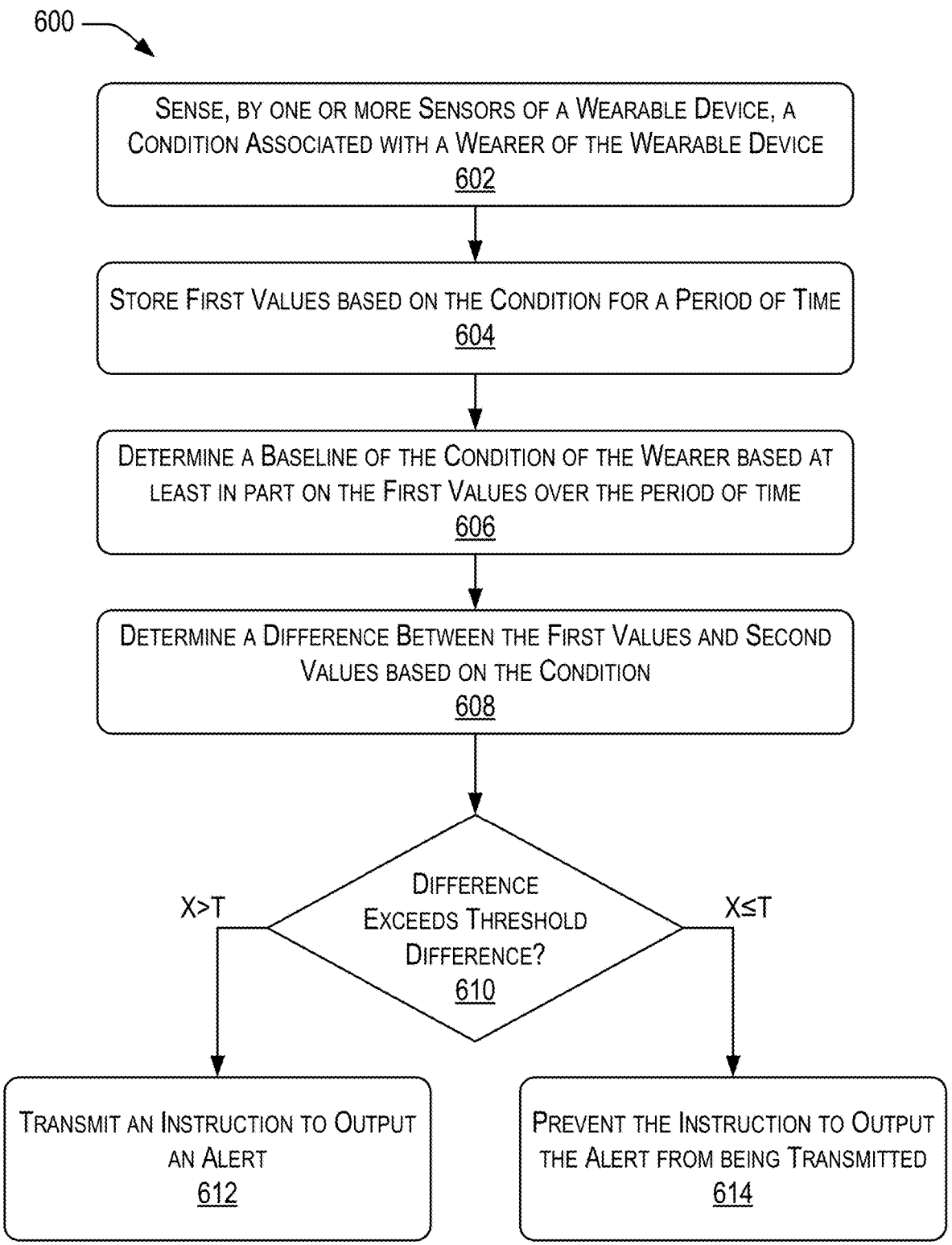
FIG. 6 is an example process for determining a baseline condition of a wearer of a wearable device, and using the baseline condition to control output of an alert, according to the techniques described herein.

FIG. 6 is an example process 600 for determining a baseline condition of a wearer of a wearable device, and using the baseline condition to control output of an alert, according to the techniques described herein. In some examples, one or more operations of the process 600 may be combined with one or more operations of the methods illustrated in FIGS. 4, 5, 7, and/or 8. In some examples, the process 600 may be performed by one or more computing devices, such as the wearable device 102 of FIG. 1, and/or a computing device of the patient management system 112 of FIG. 1.

At operation 602, the process can include sensing, by one or more sensors of a wearable device, a condition associated with a wearer of the wearable device. As discussed above, the condition may include heart rate, respiratory rate, sleep patterns, blood glucose readings, blood pressure, movement, and so forth.

At operation 604, the process can include storing, by the wearable device, first values based on the condition for a period of time. Similar to the discussion above, the period of time may be a predetermined period of time (e.g., one day, three days, one week, one month, etc.), and/or may be a variable period of time, such as between clinician visits, until an instruction to stop storing the values is received from the wearer or a clinician, until a condition is met (e.g., the values correspond to a baseline for the wearer), and so on.

At operation 606, the process can include determining, by the wearable device, a baseline of the condition of the wearer based at least in part on the first values over the period of time. The wearable device may determine the baseline condition, in some examples, over an entirety of the period of time, and/or may determine the baseline condition with respect to different activities performed by the wearer (e.g., a baseline during sleep, a baseline after meals, a baseline during/after exercise, etc.). In some examples, the baseline may correspond to the condition of the wearer prior to the wearer entering a healthcare establishment.

At operation 608, the process can include determining, by the wearable device, a difference between the first values and second values based on the condition. For instance, the second values may be received after the wearer has entered a healthcare establishment from the wearable device and/or a healthcare establishment device, as discussed above. In but one specific example, the wearer may be having a planned surgery at a hospital. The wearer may wear the wearable device for a period of time prior to the planned surgery (e.g., one week, one month, etc.) to generate baseline data associated with one or more conditions of the wearer. The wearer may continue to wear the wearable device during and/or after the surgery in a post-operative environment, continuing to sense the condition of the wearer as the wearer undergoes and recovers from the surgery. In some cases, once the values return to the baseline values for the one or more conditions specific to the wearer, the wearer may be considered ready for discharge from the hospital.

At operation 610, the process can include determining, by the wearable device, if the difference exceeds a threshold difference. In but one specific example, the wearable device may determine a baseline heart rate for a wearer while at rest prior to entering a healthcare establishment. The wearable device may compare the resting heart rate specific to the wearer to a currently-measured heart rate of the wearer while in a hospital or other healthcare establishment to determine whether the heart rate of the wearer is normal for the wearer.

At operation 612, if the wearable device determines that the difference does exceed the threshold difference, the process can include transmitting, by the wearable device, an instruction to output an alert. At operation 614, if the wearable device determines that the difference is less than or equal to the threshold difference, the process can include preventing, by the wearable device, the instruction to output the alert from being transmitted. As noted above, a patient management system may control output of alerts based on an estimated error in condition monitoring by the wearable device and/or the sensing device, a severity of the condition of the wearer (e.g., which clinician to send an alert to, such as a doctor, a nurse, a nurse assistant, etc.), activity by the wearer that may cause an expected change to the condition (but would otherwise cause output of an alert), and so forth. Continuing with the above example of comparing heart rate measurements, if the patient management system determines that the difference in the heart rate measurements exceeds a threshold difference, the patient management system may transmit an instruction to output an alert to a nurse or other clinician to check on a condition of the wearer. However, if the patient management system determines that the difference in the heart rate measurements is less than or equal to the threshold difference, the patient management system may prevent the instruction from being output to a clinician device, thus reducing unnecessary "false alerts" and allowing clinicians to focus care on those who need it.

Figure 7:
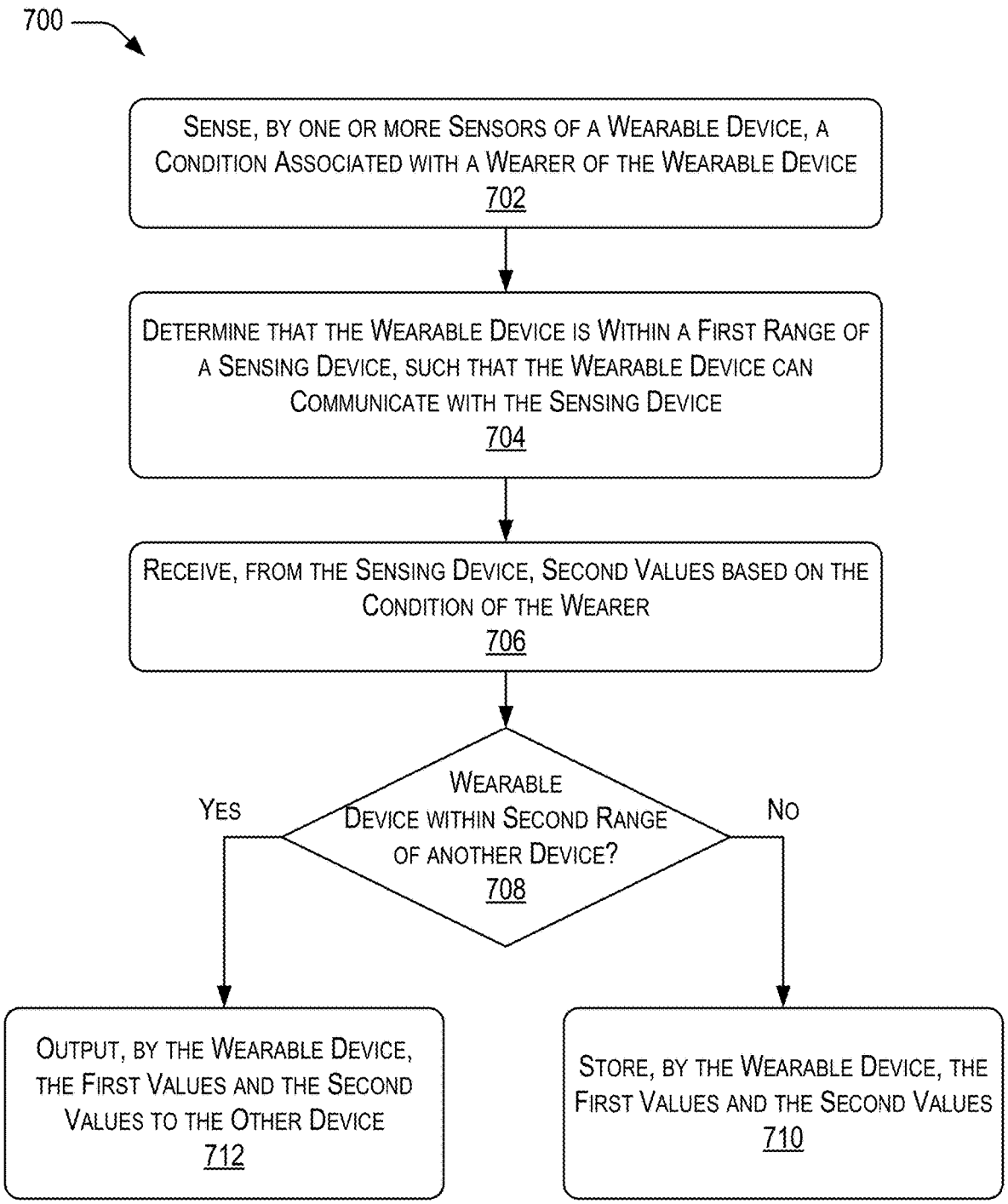
FIG. 7 is an example process for sharing data between a wearable device, a sensing device, and another device, according to the techniques described herein.

FIG. 7 is an example process 700 for sharing data between a wearable device, a sensing device, and another device, according to the techniques described herein. In some examples, one or more operations of the process 700 may be combined with one or more operations of the methods illustrated in FIGS. 4, 5, 6, and/or 8. In some examples, the process 700 may be performed by one or more computing devices, such as the wearable device 102 of FIG. 1, and/or a computing device of the patient management system 112 of FIG. 1.

At operation 702, the process can include sensing, by one or more sensors of a wearable device, a condition associated with a wearer of the wearable device. As discussed above, the condition may include heart rate, respiratory rate, sleep patterns, blood glucose readings, blood pressure, movement, and so forth.

At operation 704, the process can include determining, by the wearable device, that the wearable device is within a first range of a sensing device, such that the wearable device can communicate with the sensing device. At operation 706, the process can include receiving, by the wearable device and from the sensing device, second values based on the condition of the wearer. For example, the sensing device may be a home healthcare device, a healthcare establishment device, and/or a clinician device, as discussed above. The wearable device may communicate with the sensing device to receive the second values using any one of the described networks and/or data sharing techniques described herein. In some examples, the wearable device may store the first values and the second values as the wearer of the wearable device moves throughout an environment, such as from the wearer's home to a healthcare establishment, between different departments of a healthcare establishment, from one healthcare establishment to another, and so on.

At operation 708, the process can include determining, by the wearable device, whether the wearable device is within a second range of another device. The other device may be a clinician device which may be located at a different healthcare establishment (or different department of a same healthcare establishment). For instance, the first data may correspond to baseline data collected before the wearer enters a healthcare establishment, and the second data may correspond to data received from a vital signs device in an intensive care unit of a hospital after the wearer experiences an event such as a stroke. The wearable device may collect and store this data, and when the wearable device determines that it is within a range of a device within a long-term care facility, share this data as appropriate with a device in the long-term care facility.

At operation 710, if the wearable device determines that the wearable device is not within the second range, the process can include storing, by the wearable device, the first values and the second values. In some examples, the wearable device may continue to store data from the sensing device after the wearer exits the healthcare establishment where the sensing device is located, such as in an EMR of the wearer.

At operation 712, if the wearable device determines that the wearable device is within the second range, the process can include outputting, by the wearable device, the first values and the second values to the other device. In some examples, the first values may represent a condition of the wearer before entering the healthcare establishment (e.g., a baseline), while the second values may represent how the condition changed following entering the healthcare establishment, e.g., as a result of an accident, injury, surgery, and the like. When the wearable device detects the other device (e.g., in a different department of the healthcare establishment), the wearable device can transfer both the baseline data and the data from the sensing device to the other device, providing a seamless transition of the wearer's data between various healthcare establishments and/or healthcare establishment departments.

Figure 8:
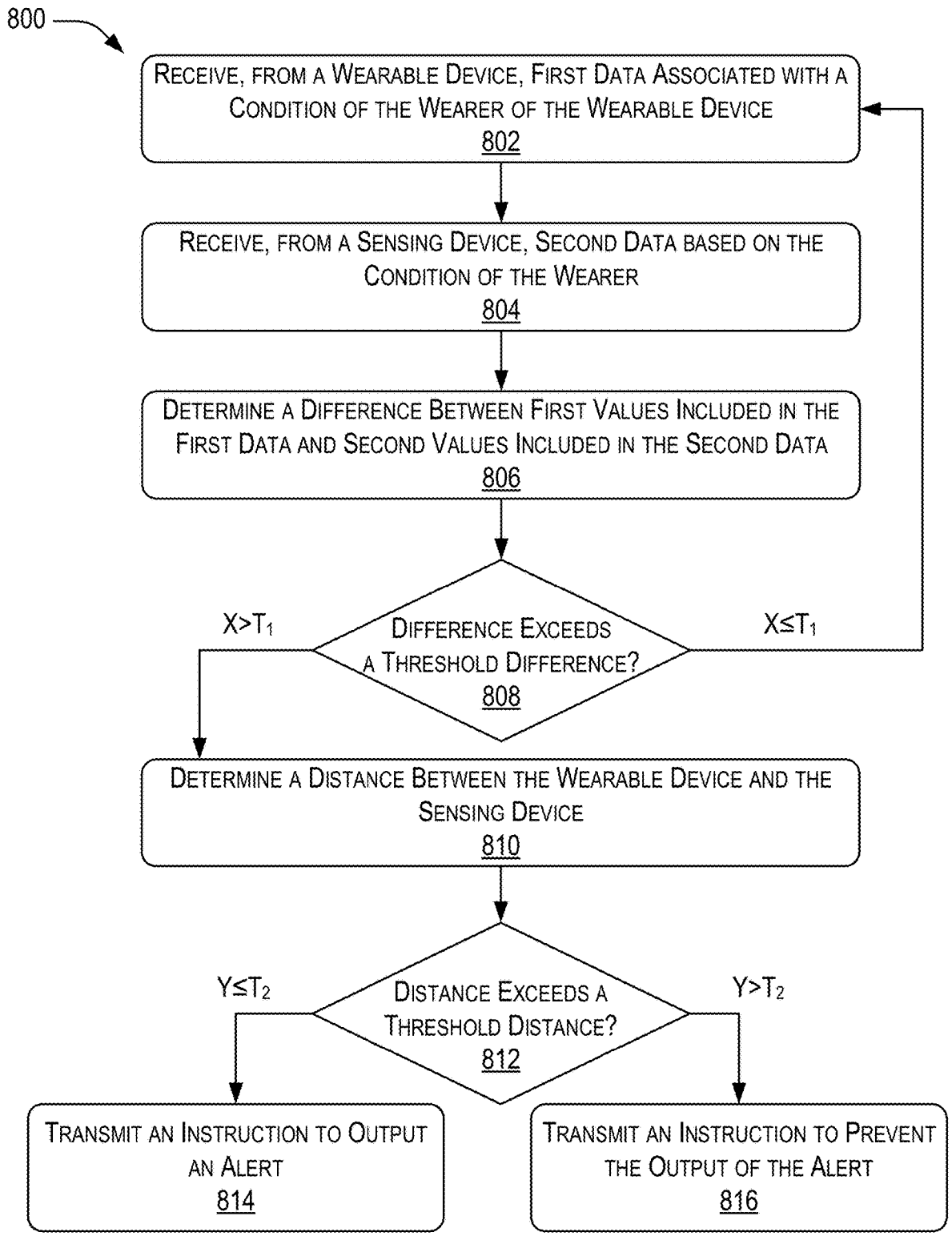
FIG. 8 is an example process for determining a difference between data received from a wearable device and data received from a sensing device, determining a distance between the wearable device and the sensing device, and using the difference and the distance to control output of an alert, according to the techniques described herein.

FIG. 8 is an example process 800 for determining a difference between data received from a wearable device and data received from a sensing device, determining a distance between the wearable device and the sensing device, and using the difference and the distance to control output of an alert, according to the techniques described herein. In some examples, one or more operations of the process 800 may be combined with one or more operations of the methods illustrated in FIGS. 4-7. In some examples, the process 800 may be performed by one or more computing devices, such as the wearable device 102 of FIG. 1, and/or a computing device of the patient management system 112 of FIG. 1.

At operation 802, the process can include receiving, by one or more processors and from a wearable device, first data associated with a condition of the wearer of the wearable device. As discussed above, the condition may include heart rate, respiratory rate, sleep patterns, blood glucose readings, blood pressure, movement, and so forth.

At operation 804, the process can include receiving, by the one or more processors and from a sensing device, second data based on the condition of the wearer. In some examples, the sensing device may be a home healthcare device, a healthcare establishment device, and/or a clinician device, as discussed above. In one specific example, the sensing device may be a hospital bed, which may sense presence of the wearer in the hospital bed, weight of the wearer, respiration of the wearer, heart rate of the wearer, and so forth.

At operation 806, the process can include determining, by the one or more processors, a difference between first values included in the first data and second values included in the second data. Continuing with the above example, if the wearer is not present in the hospital bed, the hospital bed may record a respiration value of zero breaths per minute for the wearer. The patient management system may compare this value to a respiration value of 18 breaths per minute for the wearer as recorded by the wearable device.

At operation 808, the process can include determining, by the one or more processors, if the difference exceeds a threshold difference. Continuing with the above example of respiration rate, the patient management system may have a threshold difference of one breath per minute, two breaths per minute, etc.

At operation 810, if the one or more processors determine that difference exceeds the threshold difference, the process can include determining, by the one or more processors, a distance between the wearable device and the sensing device. The wearable device and/or the sensing device may determine the distance between one another by determining if the devices are capable of communication via one or more networks, and/or the wearable device may utilize location-based services and/or GPS to determine its own location relative to the sensing device. Otherwise, in some examples, the process may return to operation 802, where the one or more processors receive data associated with the condition of the wearer is from the wearable device.

At operation 812, the process can include determining, by the one or more processors, if the distance exceeds a threshold distance. In some cases, the threshold distance may be the wearer being located within the hospital bed, within a hospital room where the hospital bed is located, a floor or department where the hospital bed is located, and so forth.

At operation 814, if the one or more processors determine that the distance is less than or equal to a threshold distance, the process can include transmitting, by the one or more processors, an instruction to output an alert. For instance, if the difference between the respiration rates as sensed by the wearable device and the hospital bed is greater than the threshold amount and the location of the wearer as indicated by the wearable device is in the hospital bed, the patient management system may output an alert to a clinician that the wearable device and/or the hospital bed are not properly sensing the respiration rate of the patient.

At operation 816, if the one or more processors determine that the distance exceeds the threshold distance, the process can include transmitting, by the one or more processors, an instruction to prevent the output of the alert. Continuing with the above example, if the difference between the respiration rates as sensed by the wearable device and the hospital bed is greater than the threshold amount and the location of the wearer as indicated by the wearable device is out of the hospital bed, the patient management system may prevent output of the alert to the clinician, as the hospital bed may not be capable of sensing the respiration rate of the wearer if the wearer is out of the bed.

Example System and Device

Figure 9:
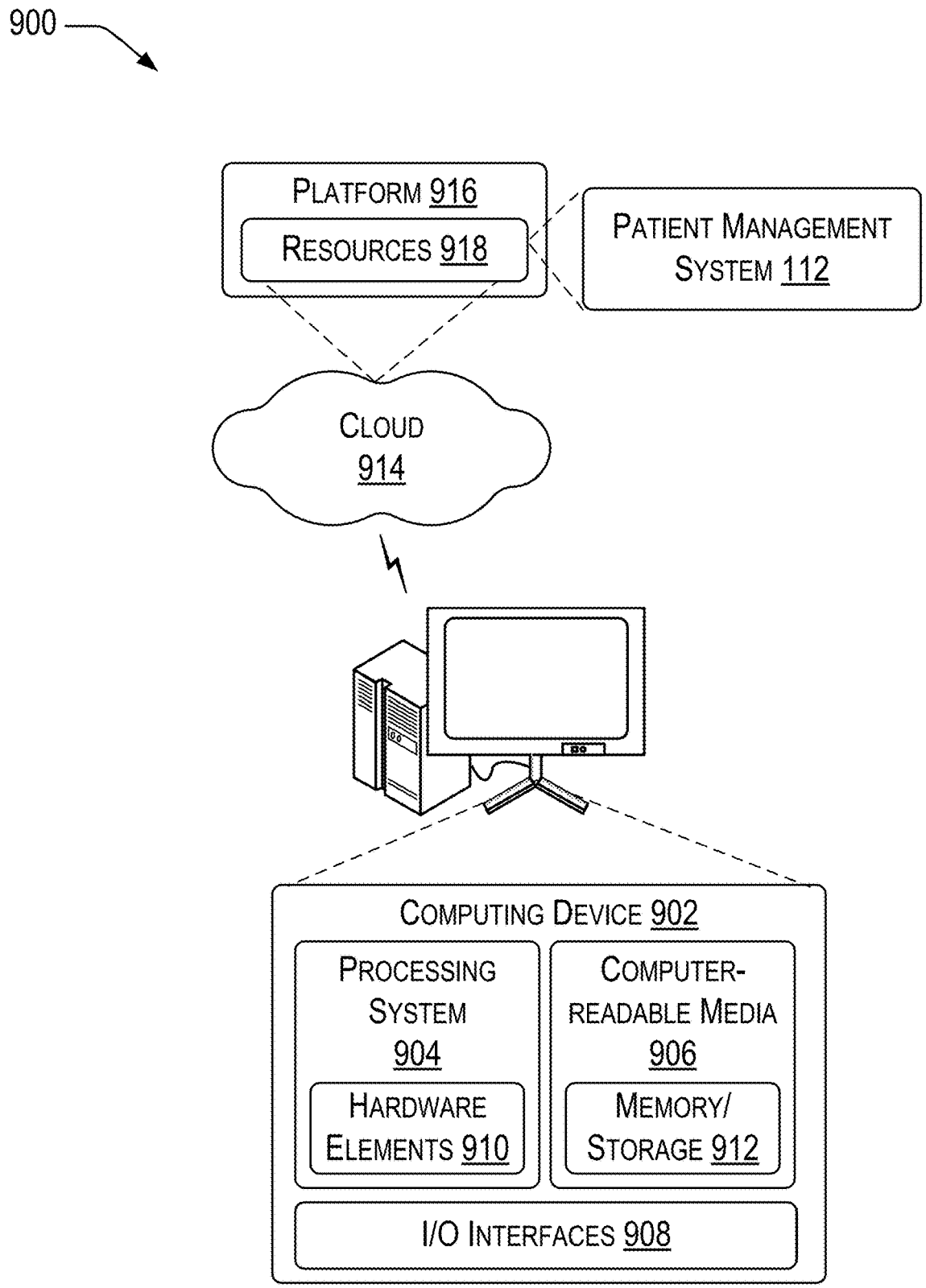
FIG. 9 depicts an example computing system and device which may be used to implement the described techniques.

FIG. 9 illustrates an example system generally at 900 that includes an example computing device 902 that is representative of one or more computing systems and/or devices that may implement the various techniques described herein. This is illustrated through inclusion of the patient management system 112. The computing device 902 may be, for example, a server of a service provider, a device associated with a client (e.g., a client device), an on-chip system, and/or any other suitable computing device or computing system.

The example computing device 902 as illustrated includes a processing system 904, one or more computer-readable media 906, and one or more I/O interface 908 that are communicatively coupled, one to another. Although not shown, the computing device 902 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 904 is representative of functionality to perform one or more operations using hardware. Accordingly, the processing system 904 is illustrated as including hardware element 910 that may be configured as processors, functional blocks, and so forth. This may include implementation in hardware as an application specific integrated circuit or other logic device formed using one or more semiconductors. The hardware elements 910 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable storage media 906 is illustrated as including memory/storage 912. The memory/storage 912 represents memory/storage capacity associated with one or more computer-readable media. The memory/storage component 912 may include volatile media (such as random access memory (RAM)) and/or nonvolatile media (such as read only memory (ROM), Flash memory, optical disks, magnetic disks, and so forth). The memory/storage component 912 may include fixed media (e.g., RAM, ROM, a fixed hard drive, and so on) as well as removable media (e.g., Flash memory, a removable hard drive, an optical disc, and so forth). The computer-readable media 906 may be configured in a variety of other ways as further described below.

Input/output interface(s) 908 are representative of functionality to allow a user to enter commands and information to computing device 902, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 902 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," "logic," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on and/or transmitted across some form of computer-readable media. The computer-readable media may include a variety of media that may be accessed by the computing device 902. By way of example, and not limitation, computer-readable media may include "computer-readable storage media" and "computer-readable transmission media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer-readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable transmission media" may refer to a medium that is configured to transmit instructions to the hardware of the computing device 902, such as via a network. Computer-readable transmission media typically may transmit computer-readable instructions, data structures, program modules, or other data in a modulated data signal, such as carrier waves, data signals, or other transport mechanism. Computer-readable transmission media also include any information delivery media. The term "modulated data signal" means a signal that has one or more of its characteristics set or changed in such a manner as to encode information in the signal. By way of example, and not limitation, computer-readable transmission media include wired media such as a wired network or direct-wired connection, and wireless media such as acoustic, radio frequency (RF), infrared, and other wireless media.

As previously described, hardware elements 910 and computer-readable media 906 are representative of modules, programmable device logic and/or device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 910. The computing device 902 may be configured to implement particular instructions and/or functions corresponding to the software and/or hardware modules. Accordingly, implementation of a module that is executable by the computing device 902 as software may be achieved at least partially in hardware, e.g., through use of computer-readable storage media and/or hardware elements 910 of the processing system 904. The instructions and/or functions may be executable/operable by one or more articles of manufacture (for example, one or more computing devices 902 and/or processing systems 904) to implement techniques, modules, and examples described herein.

The techniques described herein may be supported by various configurations of the computing device 902 and are not limited to the specific examples of the techniques described herein. This functionality may also be implemented all or in part through use of a distributed system, such as over a "cloud" 914 via a platform 916 as described below.

The cloud 914 includes and/or is representative of a platform 916 for resources 918. The platform 916 abstracts underlying functionality of hardware (e.g., servers) and software resources of the cloud 914. The resources 918 may include applications and/or data that can be utilized while computer processing is executed on servers that are remote from the computing device 902. Resources 918 can also include services provided over the Internet and/or through a subscriber network, such as a cellular or Wi-Fi network.

The platform 916 may abstract resources and functions to connect the computing device 902 with other computing devices. The platform 916 may also be scalable to provide a corresponding level of scale to encountered demand for the resources 918 that are implemented via the platform 916. Accordingly, in an interconnected device embodiment, implementation of functionality described herein may be distributed throughout multiple devices of the system 900. For example, the functionality may be implemented in part on the computing device 902 as well as via the platform 916 which may represent a cloud computing environment 914.

The example systems and methods of the present disclosure overcome various deficiencies of known prior art devices. Other embodiments of the present disclosure will be apparent to those skilled in the art from consideration of the specification and practice of the disclosure contained herein. It is intended that the specification and examples be considered as example only, with a true scope and spirit of the present disclosure being indicated by the following claims.

What is claimed is:

1. A method comprising:
    storing by a wearable device a medical history of a wearer of the wearable device;
    sensing, by one or more sensors integrated as part of the wearable device, a condition associated with the wearer;
    storing, by the wearable device and based on sensing the condition, first values, received from the one or more sensors, indicative of the condition for a period of time;
    determining, by the wearable device and based on the stored first values, baseline values corresponding to the condition;
    determining, by the wearable device and based on sensing second values and the baseline values, a set of changed baseline values corresponding to the condition;
    determining, based on a location of the wearable device, that the wearable device is within a range of a device associated with a healthcare establishment and is able to communicate with the device;
    based on determining that the wearable device is within the range, outputting, by the wearable device, the medical history to the device;
    receiving, based on outputting the medical history to the device, third values from the device associated with the condition;
    determining, by the wearable device, and based on the location, the set of changed baseline values, and the third values, context information associated with the set of changed baseline values; and
    controlling, by the wearable device, an output of an alert by a clinician device based on the context information, wherein controlling the output comprises determining whether to transmit or refrain from transmitting an executable instruction to the clinician device, the executable instruction causing the clinician device to output the alert.

2. The method of claim 1, wherein the medical history comprises information associated with a dosage of the medication and a time that the dosage was taken by the wearer.

3. The method of claim 1, further comprising:
    determining a difference between fourth values indicative of the condition and the first values;
    determining that the difference exceeds a threshold difference; and
    based on determining that the difference exceeds the threshold difference, transmitting the executable instruction to the clinician device, the executable instruction causing the clinician device to output the alert indicative of the condition.

4. The method of claim 1, wherein the period of time is a first period of time, the method further comprising:
    determining a first trend associated with the baseline values of the condition;
    determining, based on the first trend and a second trend corresponding to a second period of time, that a difference between the first trend and the second trend exceeds a threshold difference; and
    transmitting the executable instruction to the clinician device, the executable instruction causing the clinician device to output the alert indicative of the condition.

5. The method of claim 1, wherein the clinician device is a first device and the range is a first range, the method further comprising:
    receiving, from the device, fourth values based on the condition of the wearer;
    storing the fourth values by the wearable device;
    determining that the wearable device is within a second range of a second device, such that the wearable device communicates with the second device; and
    based on determining the wearable device is within the second range, outputting, by the wearable device, the first values and the fourth values to the second device.

6. The method of claim 1, wherein the clinician device is a first device, the method further comprising:
    receiving, from the device, fourth values based on the condition of the wearer;
    storing the fourth values by the wearable device;
    determining, based on the first values and the fourth values a difference between the first values and the fourth values;
    determining that the difference between the first values and the third values exceeds a threshold difference; and
    transmitting a second executable instruction to a second device, the second executable instruction causing the second device to output a second alert based at least in part on the difference exceeding the threshold difference.

7. The method of claim 1, wherein:
the period of time corresponds to a time prior to the wearer entering the healthcare establishment,
the device is located within the healthcare establishment, and
wherein determining that the wearable device is within the range of the device is based at least in part on the wearer entering the healthcare establishment.

8. The method of claim 1, wherein the condition includes one or more of heart rate, respiration, blood pressure, blood glucose, sleep patterns, exercise patterns, eating patterns, or medication consumption, the method further comprising:
receiving, from the device, an electronic medical record;
determining, by the wearable device and based on the electronic medical record, an accuracy of the one or more sensors;
calibrating, by the wearable device and based on the accuracy, the one or more sensors; and
determining, by the wearable device and based on the electronic medical record, baseline values corresponding to the condition.

9. The method of claim 1, wherein determining that the wearable device is within the range of the device includes at least one of:
detecting, by the wearable device, one or more networks associated with the device;
determining, using a GPS sensor of the wearable device, a location associated with the wearable device; or
detecting, by one or more second sensors of the wearable device, the device in proximity to the wearable device.

10. The method of claim 1, wherein the set of changed baseline values correspond to an elevated heart rate, the context information indicates the wearer is moving, and the elevated heart rate is an expected change based on movement of the wearer, the method further comprising:
based at least in part on the context information, refraining, by the wearable device, from transmitting the executable instruction to the clinician device.

11. A wearable device, comprising:
one or more sensors supported by a housing of the wearable device;
one or more processors operably connected to the one or more sensors; and
computer readable media storing instructions that, when executed by the one or more processors, cause the wearable device to perform operations comprising:
storing a medical history of a wearer of the wearable device;
sensing, by the one or more sensors of the wearable device, a condition associated with the wearer;
storing, based on sensing the condition, first values, received from the one or more sensors, indicative of the condition for a period of time;
determining, based on the stored first values, baseline values corresponding to the condition;
determining, based on sensing second values and the baseline values, a set of changed baseline values corresponding to the condition;
determining, based on a location of the wearable device, that the wearable device is within a range of a device associated with a healthcare establishment and is able to communicate with the device;
based on determining that the wearable device is within the range, outputting the medical history to the device;
receiving, based on outputting the medical history to the device, third values from the device associated with the condition;
determining, based on the location, the set of changed baseline values, and the third values, context information associated with the set of changed baseline values; and
controlling an output of an alert by a clinician device based on the context information, wherein controlling the output comprises determining whether to transmit or refrain from transmitting an executable instruction to the clinician device, the executable instruction causing the clinician device to output the alert.

12. The wearable device of claim 11, wherein the medical history comprises information associated with a dosage of the medication and a time that the dosage was taken by the wearer.

13. The wearable device of claim 11, the operations further comprising:
determining a difference between fourth values indicative of the condition and the first values;
determining that the difference exceeds a threshold difference; and
based on determining that the difference exceeds the threshold, transmitting the executable instruction to the clinician device, the executable instruction causing the clinician device to output the alert indicative of the condition.

14. The wearable device of claim 11, wherein the period of time is a first period of time, the operations further comprising:
determining a first trend associated with the baseline values of the condition;
determining, based on the first trend and a second trend corresponding to a second period of time, that a difference between the first trend and the second trend exceeds a threshold difference; and
transmitting the executable instruction to the clinician device, the executable instruction causing the clinician device to output the alert indicative of the condition.

15. The wearable device of claim 11, wherein the clinician device is a first device and the range is a first range, the operations further comprising:
receiving, from the device, fourth values based on the condition of the wearer;
storing the fourth values;
determining that the wearable device is within a second range of a second device, such that the wearable device communicates with the second device; and
based on determining the wearable device is within the second range, outputting the first values and the fourth values to the second device.

16. The wearable device of claim 11, wherein the clinician device is a first device, the operations further comprising:
receiving, from the device, fourth values based on the condition of the wearer;
storing the fourth values;
determining, based on the first values and the fourth values a difference between the first values and the fourth values;
determining that the difference between the first values and the third values exceeds a threshold difference; and
transmitting a second executable instruction to a second device, the second executable instruction causing the second device to output a second alert based at least in part on the difference exceeding the threshold difference.

17. The wearable device of claim 11, wherein:
the period of time corresponds to a time prior to the wearer entering the healthcare establishment,
the device is located within the healthcare establishment, and
determining that the wearable device is within the range of the device is based at least in part on the wearer entering the healthcare establishment.

18. The wearable device of claim 11, wherein determining that the wearable device is within the range of the device includes at least one of:
   detecting one or more networks associated with the device;
   determining, using a GPS sensor of the wearable device, a location associated with the wearable device; or
   detecting, by one or more second sensors of the wearable device, the device in proximity to the wearable device.

19. The wearable device of claim 11, wherein the set of changed baseline values correspond to an elevated heart rate, the context information indicates the wearer is moving, and the elevated heart rate is an expected change based on movement of the wearer, the operations further comprising:
   based at least in part on the context information, refraining from transmitting the executable instruction to the clinician device.

20. A non-transitory computer-readable media storing instructions that, when executed by a processor, cause the processor to perform operations comprising:
   storing by a wearable device a medical history of a wearer of the wearable device;
   sensing, by one or more sensors integrated as part of the wearable device, a condition associated with the wearer;
   storing, by the wearable device and based on sensing the condition, first values, received from the one or more sensors, indicative of the condition for a period of time;
   determining, by the wearable device and based on the stored first values, baseline values corresponding to the condition;
   determining, by the wearable device and based on sensing second values and the baseline values, a set of changed baseline values corresponding to the condition;
   determining, based on a location of the wearable device, that the wearable device is within a range of a device associated with a healthcare establishment and is able to communicate with the device;
   based on determining that the wearable device is within the range, outputting, by the wearable device, the medical history to the device;
   receiving, based on outputting the medical history to the device, third values from the device associated with the condition;
   determining, by the wearable device, and based on the location, the set of changed baseline values, and the third values, context information associated with the set of changed baseline values; and
   controlling, by the wearable device, an output of an alert by a clinician device based on the context information, wherein controlling the output comprises determining whether to transmit or refrain from transmitting an executable instruction to the clinician device, the executable instruction causing the clinician device to output the alert.

* * * * *